(12) United States Patent
Lewallen et al.

(10) Patent No.: US 7,758,342 B2
(45) Date of Patent: Jul. 20, 2010

(54) DETECTING AND INDICATING A PROXIMITY OF A DENTAL INSTRUMENT TO A TOOTH APICAL FORAMEN

(75) Inventors: Scott Lewallen, Duvall, WA (US); Daniel Thacker, Snohomish, WA (US)

(73) Assignee: Aseptico, Inc., Woodinville, WA (US)

( * ) Notice: Subject to any disclaimer, the term of this patent is extended or adjusted under 35 U.S.C. 154(b) by 1204 days.

(21) Appl. No.: 10/772,104

(22) Filed: Feb. 4, 2004

(65) Prior Publication Data
US 2004/0158169 A1    Aug. 12, 2004

Related U.S. Application Data

(63) Continuation-in-part of application No. 10/205,966, filed on Jul. 26, 2002, now Pat. No. 6,845,265.

(51) Int. Cl.
A61C 1/00  (2006.01)
A61C 19/04 (2006.01)
A61C 5/00  (2006.01)

(52) U.S. Cl. ................ 433/27; 433/72; 433/215

(58) Field of Classification Search ........... 433/27, 433/72, 215; 600/547
See application file for complete search history.

(56) References Cited

U.S. PATENT DOCUMENTS

| | | | |
|---|---|---|---|
| 3,916,529 A | 11/1975 | Mousseau | |
| 3,993,044 A | 11/1976 | McGuffin | |
| 4,243,388 A * | 1/1981 | Arai | 433/27 |
| 4,273,531 A | 6/1981 | Hasegawa | |
| 4,353,693 A * | 10/1982 | Dery et al. | 433/27 |
| 4,447,206 A | 5/1984 | Ushiyama | |
| 4,526,179 A | 7/1985 | Salesky | |
| 5,017,134 A | 5/1991 | Saito | |

(Continued)

FOREIGN PATENT DOCUMENTS

EP    0392518 A1    10/1990

(Continued)

OTHER PUBLICATIONS

PCT/US2005/003783 Search Report; published Jun. 6, 2005 to Aseptico.

*Primary Examiner*—Cris L Rodriguez
*Assistant Examiner*—Heidi M Eide
(74) *Attorney, Agent, or Firm*—Janeway Patent Law PLLC; John Janeway

(57) ABSTRACT

An apparatus that indicates a proximity of a dental instrument in a tooth's root canal to the canal's apical foramen while using the dental instrument to perform a dental/medical procedure. The apparatus includes a signal generator that provides divider signal across a first node and a third node, and a reference impedance coupled between the first node and a second node. The second node and third node include configuration for electrically coupling between a tip of the dental instrument and an electrode coupled with a body tissue of the patient, a stimulation signal being defined across the second node and the third node. The apparatus also includes a microprocessor operable to compare the stimulation signal and the divider signal, and generate a proximity signal in response to the comparison, and a proximity indicator that indicates the proximity of the dental instrument to the apical foramen in response to the proximity signal.

37 Claims, 4 Drawing Sheets

U.S. PATENT DOCUMENTS

| | | |
|---|---|---|
| 5,049,069 A | 9/1991 | Salesky |
| 5,080,586 A | 1/1992 | Kawai |
| 5,211,556 A | 5/1993 | Kobayashi et al. |
| 5,267,997 A * | 12/1993 | Farin et al. .................... 606/38 |
| 5,295,833 A | 3/1994 | Chihiro et al. |
| 5,759,159 A * | 6/1998 | Masreliez .................... 600/547 |
| 5,902,105 A | 5/1999 | Uejima et al. |
| 6,059,569 A | 5/2000 | Otsuka |
| 6,356,350 B1 * | 3/2002 | Silver et al. .................. 356/437 |
| 6,425,875 B1 | 7/2002 | Reifman et al. |

FOREIGN PATENT DOCUMENTS

| | | |
|---|---|---|
| EP | 1384449 A1 | 1/2004 |
| EP | 1444966 A1 | 8/2004 |
| FR | 2741524 | 5/1997 |
| WO | WO 2004/105631 A1 | 12/2004 |

* cited by examiner

DETECTING AND INDICATING A PROXIMITY OF A DENTAL INSTRUMENT TO A TOOTH APICAL FORAMEN

PRIORITY

The present application is a continuation-in-part of, and claims priority from, U.S. patent application Ser. No. 10/205,966, filed Jul. 26, 2002, and issued 18 Jan. 2005 as U.S. Pat. No. 6,845,265, which is incorporated herein by reference for all purposes.

BACKGROUND

FIG. 1 illustrates a cross-sectional view of a tooth, with several parts of the tooth identified. Many dental or medical procedures, such as cleaning non-vital nerves and blood vessels from a root canal, require that a dental/medical practitioner know the location of the opening of an apex of a patient's tooth. The apex is the tip of the root, and it has an opening or passage where nerve, blood supply, and other tissue leave the jawbone and enter the tooth's root canal. The opening is commonly referred to as the apical foramen. These dental/medical procedures typically involve inserting and using or operating a dental instrument, such as a file or other tool, to remove tissue from the canal. It is important that the position of the tip of the dental instrument be known relative to the apical foramen to minimize tissue damage. Throughout this specification, a "dental instrument" includes any device inserted into a tooth for direct or indirect treatment, including but not limited to reamers, files, and like instruments used to clean out tissue contained in a tooth's root canal, to fix anchors into the tooth, to insert syringe needles and other devices into the tooth, and the like. The dental instrument includes an electrically conductive portion along at least a part of its length.

For example, if the dental/medical practitioner does not clear a root canal by inserting the file or other tool all the way to the apical foramen, nerve, vascular and other tissue can remain in the tooth's root canal. This remaining tissue can become infected and create problems for the patient. If the dental/medical practitioner penetrates the apical foramen, healthy nerve, vascular, and other tissue can be damaged. Such damage can cause unnecessary pain for the patient. Consequently, a number of methods and devices have been developed to help the dental/medical practitioner determine the location of the apical foramen of a specific tooth.

One such method and device includes taking numerous radiographs, such as x-rays with an x-ray machine, of a patient's tooth while the dental/medical practitioner moves a dental tool in the root canal. Unfortunately, this method subjects the patient to multiple exposures of radiation as the dental/medical practitioner moves the dental tool toward the apical foramen. This method can also be very time consuming because the dental/medical practitioner does not move the dental tool while the patient's tooth is radiographed and the radiographs developed. This method can also fail to show the location of the apical foramen relative to a dental tool if the tooth cannot be isolated on a radiograph.

Another such method and device includes electronically detecting the apical foramen's location by measuring changes in impedance (resistance and capacitance) between an electrode in a patient's tooth (often the dental instrument) and an electrode attached to the patient's lip. Typically, a stimulus voltage applied across these electrodes includes two or more signals. One signal has a high frequency while the other signal has a low frequency. Since the capacitive portion of an impedance is a function of signal frequency, impedances at the two frequencies are compared to estimate the capacitive portion. By monitoring changes in the impedance associated with each signal as the dental/medical practitioner moves the tool in the root canal, the dental/medical practitioner can be provided an approximate location of the tooth's apical foramen relative to the tool tip.

With this method, the practitioner must stop the operation of the handpiece to eliminate the electrical noise, maintain the position of the dental instrument in the root canal, attach a lead of an electronic detector to the dental instrument, read the proximity of the dental instrument's tip to the apical foramen, disconnect the lead, and resume operation until another proximity indication is desired, when the process is repeated. Dental/medical practitioners would like to know the proximity of the tip to the apical foramen in real time as they move the tip of the dental instrument down the root canal, particularly when driving the dental instrument with an electrically operated handpiece. Attempts have been made to eliminate the several steps of individually connecting and disconnecting the lead to the dental instrument by externally mounting the electronic detector lead on the handpiece, and coupling the lead by a brush to the dental instrument. Such systems require a custom or retrofitted handpiece, and still require an extra wire. In addition, noise immunity of these systems during handpiece operation has not been established.

Coupling proximity indication circuitry to existing electrically conductive handpiece pathways has encountered problems with electrical noise. Operation of the handpiece creates electrical noise, such as make and break of conductive gears, gears turning, PWM motor drivers, a metal motor, and other equipment. Direct current, which may be more noise immune, should not be used because of possible adverse biological consequences. Existing techniques measure the real component of a proximity-detecting signal (also referred to as "stimulation signal") passing through a tooth by measuring the peak components of this signal. However, noise from the dental handpiece adds to the peak values and distorts the signal readings, or the signal peaks drift. Existing methods work well only when the dental handpiece is off, and noise from the dental handpiece is absent.

SUMMARY

An aspect of the invention provides a device, system, and method for indicating the proximity of a dental instrument in a tooth's root canal to the canal's apical foramen while using the dental instrument to perform a dental/medical procedure.

An embodiment of the present invention provides an apparatus that includes a signal generator that provides a divider signal across a first node and a third node, and a reference impedance coupled between the first node and a second node. The second node and third node are configured for electrically coupling between the tip of the dental instrument and an electrode coupled with a body tissue of the patient, a stimulation signal being defined across the second node and the third node. The apparatus also includes a microprocessor operable to compare the stimulation signal and the divider signal, and generate a proximity signal from a correlation parameter in response to the comparison, and a proximity indicator that indicates the proximity of the tip of the dental instrument to the apical foramen in response to the proximity signal. The signal generator may generate a single frequency divider signal, and the stimulation signal may include noise generated by a handpiece driving the dental instrument. The correlation parameter may include a lookup table, or an equation.

Another embodiment of the present invention provides a method for generating a divider signal across a first node and a third node, impeding a current with a reference impedance coupled between the first node and a second node, and further impeding the current by electrically coupling the tip of the dental instrument in the root canal and an electrode coupled with a body tissue of the patient between the second node and third node, a stimulation signal being defined between the second node and the third node. The method further includes sampling and demodulating the stimulation signal, digitally comparing the demodulated stimulation signal and the divider signal, and generating a proximity signal from a stored lookup table in response to the comparison, the lookup table correlating at least one comparison of the divider signal and the stimulation signal with a proximity of the tip of the dental instrument in a root canal to the apical foramen, and indicating a proximity of the tip of the dental instrument to the apical foramen in response to the proximity signal. These and various other features as well as advantages of the present invention will be apparent from a reading of the following detailed description and a review of the associated drawings.

BRIEF DESCRIPTION OF THE DRAWINGS

The features of the present invention which are believed to be novel are set forth with particularity in the appended claims. Aspects of the invention, together with advantages thereof, may best be understood by making reference to the following description taken in conjunction with the accompanying drawings, in the several figures of which like referenced numerals identify like elements, and wherein:

DETAILED DESCRIPTION

In the following detailed description of exemplary embodiments of the invention, reference is made to the accompanying drawings, which form a part hereof. The detailed description and the drawings illustrate specific exemplary embodiments by which the invention may be practiced. These embodiments are described in sufficient detail to enable those skilled in the art to practice the invention. It is understood that other embodiments may be utilized, and other changes may be made, without departing from the spirit or scope of the present invention. The following detailed description is therefore not to be taken in a limiting sense, and the scope of the present invention is defined by the appended claims.

Figure 1:
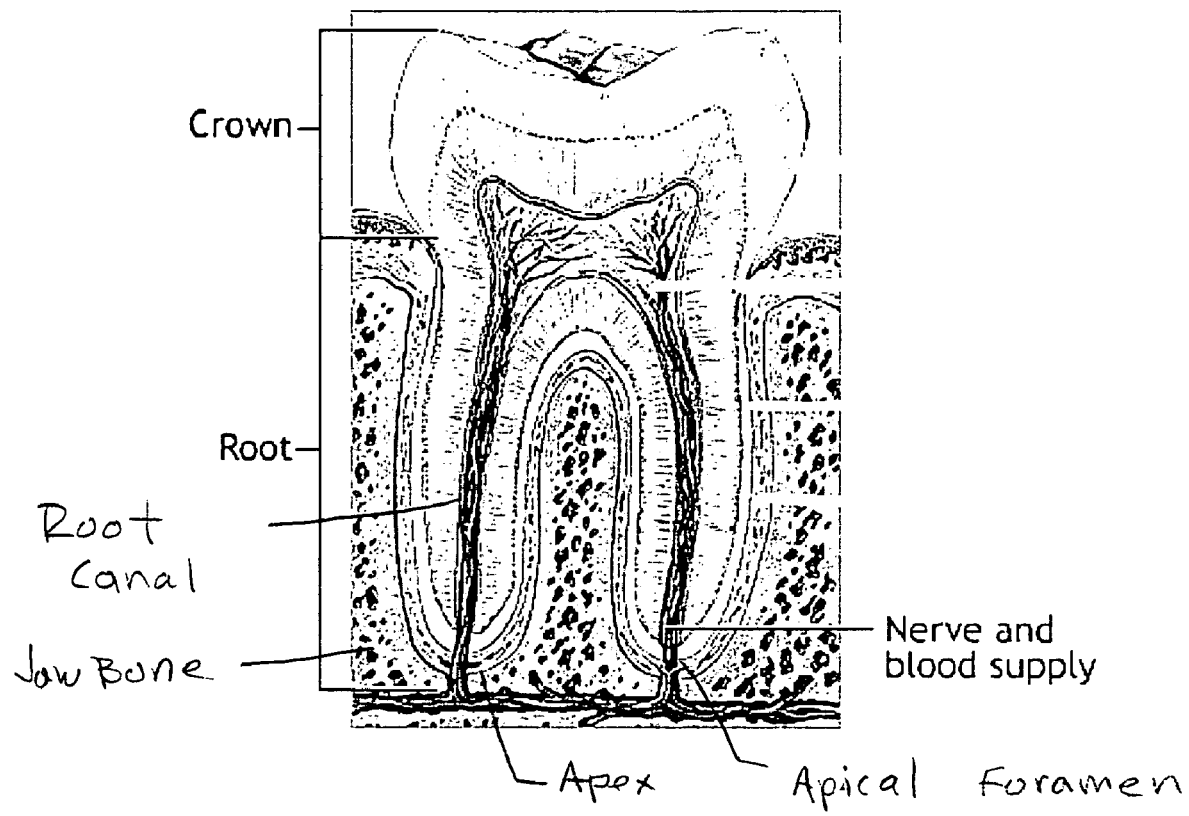
FIG. 1 illustrates a cross-sectional view of a tooth, with several parts of the tooth identified.
Figure 2:
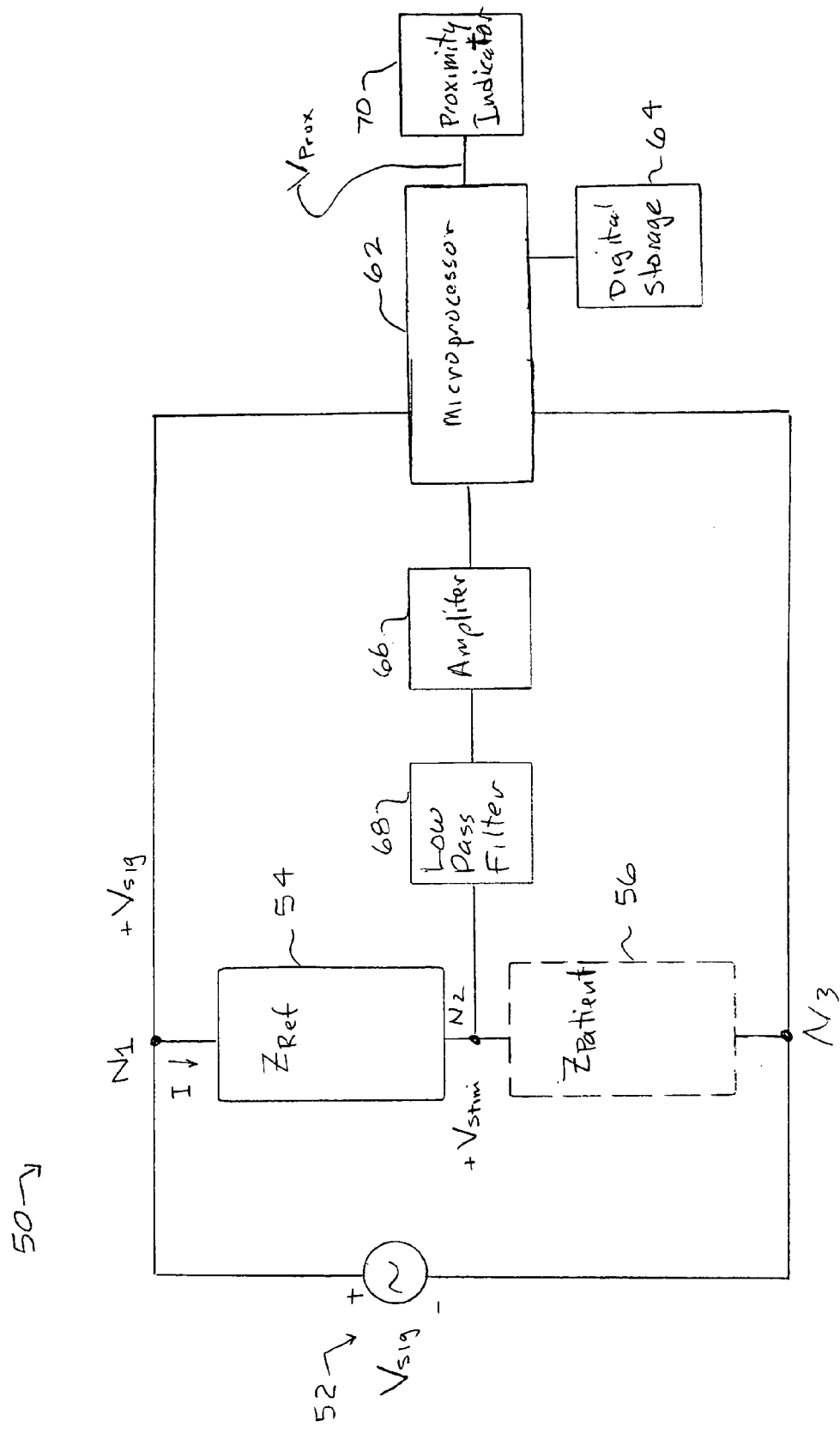
FIG. 2 illustrates a functional block diagram of an apparatus that indicates the proximity of a tip of a dental instrument in a tooth's root canal to the canal's apical foramen, according to an embodiment of the invention.

FIG. 2 illustrates a functional block diagram of an apparatus 50 that can indicate the proximity of a tip (not shown) of a dental instrument (not shown) in a tooth's root canal to the canal's apical foramen while using the dental instrument, according to an embodiment of the invention. The apparatus 50 indicates the proximity of the tip to the apical foramen by sensing the impedance of a patient between the tip and another electrode, such as a clip (shown and discussed in FIG. 4) fastened to the patient's lip. The apparatus 50 includes a signal generator 52 to generate a divider signal $V_{sig}$ across a first node $N_1$ and a third node $N_3$; and a microprocessor 62 to sample and demodulate a stimulation signal $V_{stim}$ that has been modified by the impedance of a patient, from noise generated by the dental instrument during the instrument's operation. By demodulating the stimulation signal from the noise, one may use the apparatus 50 to determine the proximity of a drill's tip, for example, that is located inside a tooth's root canal to the canal's apical foramen while one uses the drill to remove soft tissue from the canal. Thus, the time required to complete such a dental/medical procedure may be reduced.

Divider Theory

An embodiment of the invention includes using an impedance voltage divider to determine an impedance of a portion of the patient's root canal between a tip of a dental instrument in the root canal and the apical foramen, which is then correlated by a lookup table to a proximity indication. The impedance divider includes the reference impedance $Z_{Ref}$ coupled between the first node $N_1$ and the second node $N_2$, and the patient impedance $Z_{Pat}$ coupled between the second node $N_2$ and the third node $N_3$. The patient impedance $Z_{Pat}$ models the patient as a Thevenin equivalent, having resistive and reactive (capacitive) elements.

The signal generator 52 provides a divider signal $V_{Sig}$ across the first node $N_1$ and the third node $N_3$. A stimulation signal $V_{Stim}$ is defined across the second node $N_2$ and the third node $N_3$.

Using Ohm's law, a current I between the first node $N_1$ and the third node $N_3$ may be analyzed as an impedance voltage divider as follows:

$$I = V_{Sig}/Z_{Total}$$

$$Z_{Total} = Z_{Ref} + Z_{Pat}$$

$$V_{Stim} = I \times Z_{Pat} = V_{sig} \times (Z_{Pat}/(Z_{Ref} + Z_{Pat}))$$

$$V_{Sig}/V_{Stim} = (Z_{Ref} + Z_{Pat})/Z_{Pat}$$

$$Z_{Pat} = Z_{Ref}((V_{Stim})/(V_{Sig} - V_{Stim}))$$

If $Z_{Ref}$ is known and $V_{Stim}$ and $V_{Sig}$ are measured, the impedance $Z_{Pat}$, which is a function of the distance between the tip of the dental instrument in the root canal and the apical foramen, can be determined. When $V_{Sig}$ and $Z_{Ref}$ are held constant, $V_{Stim}$ changes as a function of $Z_{Pat}$, with $Z_{Pat}$ changing in response to changes in position of the tip of the dental instrument in the root canal.

Components

Still referring to FIG. 2, the signal generator 52 outputs the divider signal $V_{Sig}$, and may be any type of alternating voltage signal generator having a measurable frequency, phase, and amplitude. The signal generator 52 may include a control loop to maintain the frequency and amplitude. The frequency may be any single frequency compatible with the other components of the apparatus 50 and the patient. For example, in one embodiment, the frequency of the divider signal may be between 500 Hz to 10 KHz. As the frequency increases into an upper part of this range, the reactive component of the patient impedance $Z_{Pat}$ becomes more significant for typical capacitance values presented between the tip of the dental tool and the lip of the patient, and in the leads. While the reactive component can be compensated for, a preference is to limit reactive behavior by using a frequency in a lower part of this range. The frequency selected preferably should not otherwise be present in the environment, such as 50-60 cycles, or a signal frequency used to operate a handpiece, such as 28K pulse-width-modulated signal. Although direct current may be used direct current should not be used because of undesirable biological consequences to the tooth.

Still referring to FIG. 2, the apparatus 50 may include signal-conditioning circuitry, also referred to as a signal conditioner, which conditions the stimulation voltage signal $V_{Stim}$ for measurement. For example, if amplification is required, the apparatus 50 optionally includes an amplifier 66, which may be any device operable to amplify the stimulation voltage signal $V_{Stim}$, if necessary, to values suitable for processing the stimulation signal $V_{Stim}$ by the microprocessor 62. For example, an amplification factor of between two and eight may be used to provide improved resolution and aid in noise filtration. By way of further example, if noise filtration is required, the apparatus 50 optionally includes a filter illustrated as the low-pass filter 68. The low-pass filter 68 may be any filter device, such as an active or passive filter, having a single transmission band extending from zero to a cutoff frequency that is above the divider signal $V_{Sig}$ frequency. The cutoff frequency may be selected in conjunction with the capabilities of the microprocessor 62 and parameters of an algorithm described below selected for demodulating noise from the stimulation signal $V_{Stim}$ with an accepted degree of accuracy. The low-pass filter 68 removes higher-order components of noise in the stimulation signal $V_{Stim}$ for more efficient demodulation. For example, the cutoff frequency may be between three and ten times the divider signal $V_{Sig}$ frequency.

The microprocessor 62 may be any microprocessor, preferably having low power consumption and advantageously used in miniaturized systems. The apparatus 50 may also include digital storage 64, which may be any digital data storage device or media for saving data in a semi-permanent or permanent form, including a memory physically associated with the microprocessor 62. The microprocessor 62 may be programmed to detect and sample the divider signal $V_{Sig}$ and the stimulation signal $V_{Stim}$ using any suitable technique known in the art, the two signals being synchronized. In an alternative embodiment, a separate analog-to-digital converter may be used to detect and sample the signals (digitize), and the digitalized signals provided to the microprocessor 62. The microprocessor 62 may be further programmed to demodulate the stimulation signal $V_{Stim}$, compare the demodulated stimulation signal $V_{Stim}$ and the divider signal $V_{Sig}$, access at least one stored lookup table, and generate a proximity signal $V_{Prox}$, indicating the locations of the dental tool relative to the apical foramen from the lookup table in response to the comparison of the demodulated stimulation signal $V_{Stim}$ and the divider signal $V_{Sig}$. In another embodiment, the microprocessor 62 may access a formula and generate the proximity signal $V_{Prox}$ from the formula. In a further alternative embodiment, the stimulation signal $V_{Stim}$ may be demodulated by an analog device with respect to the divider signal $V_{Sig}$, and the demodulated divider signal $V_{Sig}$ provided to the microprocessor 62 for comparison.

The digital storage 64 may include at least one stored lookup table that correlates at least one comparison of the divider signal $V_{Sig}$ and the stimulation signal $V_{Stim}$ with the proximity of the tip of the dental instrument in a root canal to the apical foramen. Additional description of the lookup table and its creation is provided below.

The demodulation process includes reconversion of the stimulation signal $V_{Stim}$ back to the original frequency of the divider signal $V_{Sig}$ by removing frequency modulations introduced by noise, typically, from an apparatus operating the dental instrument. The demodulation process also includes determining phase and amplitude of the stimulation signal $V_{Stim}$. The demodulation process executed by the microprocessor 62 removes noise from the stimulation signal $V_{Stim}$ using techniques known in the art to digitally remove noise from a data signal. These techniques include, but are not limited to, application of at least one of the following: a synchronous demodulation algorithm, a fast Fourier transform, a single frequency fast Fourier transform, and a convolving algorithm. The demodulation process may include sampling the stimulation signal $V_{Stim}$ at a selected rate greater than the Nyquist frequency of the anticipated noise component of the stimulation signal $V_{Stim}$. If for example, noise generated by the dental handpiece is generally below 5 KHz, a divider voltage signal $V_{Sig}$ of 1 KHz may be selected, the low-pass filter 68 may be selected with a cutoff frequency of 5 KHz, and a sampling rate of 12 KHz may be selected to provide sampling of the noise frequency range of 0-5 KHz at slightly greater than the Nyquist frequency. The demodulation algorithm rejects frequencies in the stimulation signal $V_{Stim}$ other than the divider voltage signal $V_{Sig}$ frequency, which in this example are frequencies other than 1 KHz.

Because the stimulation signal $V_{Stim}$ and the divider voltage signal $V_{Sig}$ are the same frequency, the comparison process requires that the phase and magnitude of each signal be known. The phase and magnitude of the stimulation signal $V_{Stim}$ can be known by design or by measurement. If the divider voltage signal $V_{Sig}$ is known by design to be accurate and stable, then the demodulated stimulation signal $V_{Stim}$ may be treated as having a known phase and magnitude. However, in one embodiment the microprocessor 62 may also demodulate the divider voltage signal $V_{Sig}$ phase and amplitude, allowing the phase and amplitude of the divider voltage signal $V_{Sig}$ at the node $N_1$ to be compared with the phase and amplitude of the demodulated stimulation signal $V_{Stim}$ at node $N_2$.

The amplitude and phase information of the stimulation signal $V_{Stim}$, are compared with the amplitude and phase of the divider signal $V_{Sig}$. The phase comparison indicates the reactive components in the patient impedance $Z_{Pat}$ and/or the reference impedance $Z_{Ref}$. During the process of generating the proximity signal, the microprocessor 62 compares relative values of the demodulated stimulation signal $V_{Stim}$ and the divider signal $V_{Sig}$. For example, assume that $Z_{Ref}$ is 2K ohms. Further assume that the patient impedance $Z_{Pat}$ equals 2K ohms when the tip of the dental instrument is at the apex, which is the generally accepted impedance between an apical foramen and an electrode coupled with the patient's lip or skin. If the ratio of the divider signal $V_{Sig}$ amplitude to the demodulated stimulation signal $V_{Stim}$ amplitude is 2:1, then according to Ohm's law, $Z_{Pat}=Z_{Ref}=2K$ ohms. This ratio indicates the tip of the dental instrument is at or approximately at the apical foramen. In the same example, if the ratio is 4:3, then $Z_{Pat}>Z_{Ref}$, and the tip of the dental instrument is located away from the apical foramen. In the above example, only the real or resistive components of $Z_{Pat}$ and $Z_{Ref}$ are compared. In furtherance of the above example, $Z_{Ref}$ may consist essentially of only a resistive member and no reactive component. In another embodiment, $Z_{Ref}$ may include a reactive component. The above ratios are illustrative of a situation where the amplitude of the stimulation signal $V_{Stim}$ has not been amplified by the amplifier 66. If the stimulation signal $V_{Stim}$ has been amplified, then the ratio numbers will change in response to the amplification. However, comparison of relative values of an amplified and demodulated stimulation signal $V_{Stim}$ and the divider signal $V_{Sig}$ continues to reflect relative values of $Z_{Pat}=Z_{Ref}$. For example, if the amplifier 66 has a gain of four, and the ratio of the divider signal $V_{Sig}$ to the amplified and demodulated stimulation signal $V_{Stim}$ is 2:4, then $Z_{Pat}=Z_{Ref}=2K$ ohms remains the case.

In a further alternative embodiment, the comparison may include comparing the phases of the synchronized demodulated stimulation signal $V_{Stim}$ and divider signal $V_{Sig}$. The patient impedance $Z_{Pat}$ illustrated in FIG. 2 includes both resistive and reactive components, the reactive component typically being capacitance. The capacitance changes the patient's impedance $Z_{Pat}$, thus, decreasing the stimulation signal $V_{Stim}$ at the second node $N_2$ and inducing a phase shift. If only the amplitudes of the stimulation signal $V_{Stim}$ and the divider signal $V_{Sig}$ were compared when a capacitive component is present in the patient impedance $Z_{Pat}$, such comparison would incorrectly indicate that there was less resistance in the patient's impedance $Z_{Pat}$ than there really is. The phase information provides the comparison process with both the resistive and capacitive components of the patient impedance $Z_{Pat}$. This can allow the comparison process to compare any phase shift between the demodulated stimulation signal $V_{Stim}$ and the divider signal $V_{Sig}$.

The proximity signal $V_{Prox}$ may be generated by the microprocessor 62 using the lookup table stored in the digital storage 64. This configuration provides flexibility in empirically establishing a proximity indication in response to the comparison of the demodulated stimulation signal $V_{Stim}$ and the divider signal $V_{Sig}$. Continuing with the above example, if the comparison ratio is 2:1, the lookup table may establish that the 2:1 ratio is indicative of a zero tip distance to the apical foramen, and generate a proximity signal $V_{Prox}$ indicating a "00" distance. Still continuing with the above example, if the comparison ratio is 4:3, the lookup table may establish the 4:3 ratio as indicative that the tip is 80 percent of the length of the root canal away from the apical foramen, and generate a proximity signal $V_{Prox}$ indicating an "80" distance.

In an alternative embodiment, the comparison may be outputted by the microprocessor 62 as the proximity signal $V_{Prox}$ to a proximity indicator 70 that may be included in the apparatus 50. In this alternative embodiment, the proximity indicator 70 includes a lookup table or other functionality that establishes a proximity indication in response to the comparison signal $V_{Prox}$.

Still referring to FIG. 2, the proximity indicator 70 may be any indicator that presents apical foramen proximity data to the dental/medical practitioner in response to the proximity signal. The proximity indicator may include a digital display. The digital display may display digits representing a relative proximity to the apical foramen, with, for example, a "99" representing initial entry of the tip of the dental instrument into a root canal from the crown portion of the tooth, a "0" representing the tip at the apical foramen, and numbers between correspondingly representing intermediate proximities. In an alternative embodiment, the proximity signal $V_{Prox}$ may be calibrated to represent a distance to the apical foramen in a unit-of-measure, and the digital display being operable to display proximity in the unit-of-measure, such as millimeters. In another embodiment, the proximity indicator may include a haptic device, such as a vibrator or sound that is activated at a proximity to the apical foramen. In a further embodiment, the proximity indicator 70 may include indicating lights. For example, an end light can represent the point where the dental instrument is at the tooth's apical foramen, or substantially close. Other lights can indicate a distance between the tip of the dental instrument and the apical foramen by their proximity to the end light. In other embodiments, the lights or digits of the display can be color-coded as desired to provide the dental/medical practitioner an easily recognizable indication of proximity to the apical foramen. Additionally or alternatively, the display can include any desired sound to indicate the distance between the tip of the tool and the apical foramen.

Connections

The apparatus 50 includes coupling one side of the divider signal $V_{Sig}$, one end of the reference impedance $Z_{Ref}$, and one divider signal $V_{Sig}$ sensing input of the microprocessor 62 to the first node N1. The apparatus 50 further includes coupling another side of the divider signal $V_{Sig}$, an end of the patient impedance $Z_{Pat}$, and another divider signal $V_{Sig}$ sensing input of the microprocessor 62 to the third node $N_3$. Another end of the reference impedance $Z_{Ref}$ and another end of the patient impedance $Z_{Pat}$ are coupled with the second node $N_2$. A stimulation voltage $V_{Stim}$ input of the microprocessor is coupled with the second node $N_2$. Optionally and preferably, the low-pass filter 68 and the amplifier 66 are coupled between the second node $N_2$ and the stimulation voltage $V_{Stim}$ input of the microprocessor 62 for processing of the stimulation voltage $V_{Stim}$ before it is received by the microprocessor. A proximity signal $V_{Prox}$ output of the microprocessor 62 is coupled with an input of the proximity indicator 70.

In an alternative embodiment, the stimulation signal $V_{Stim}$ may be supplied to the second node $N_2$ by any signal source. For example, an alternating current source that generates a known, accurate, and stable current may be used in place of the divider signal $V_{Sig}$ and the reference impedance $Z_{Ref}$. With a known current, the patient impedance $Z_{Pat}$ will be a function of the stimulation signal $V_{Stim}$.

Figure 3:
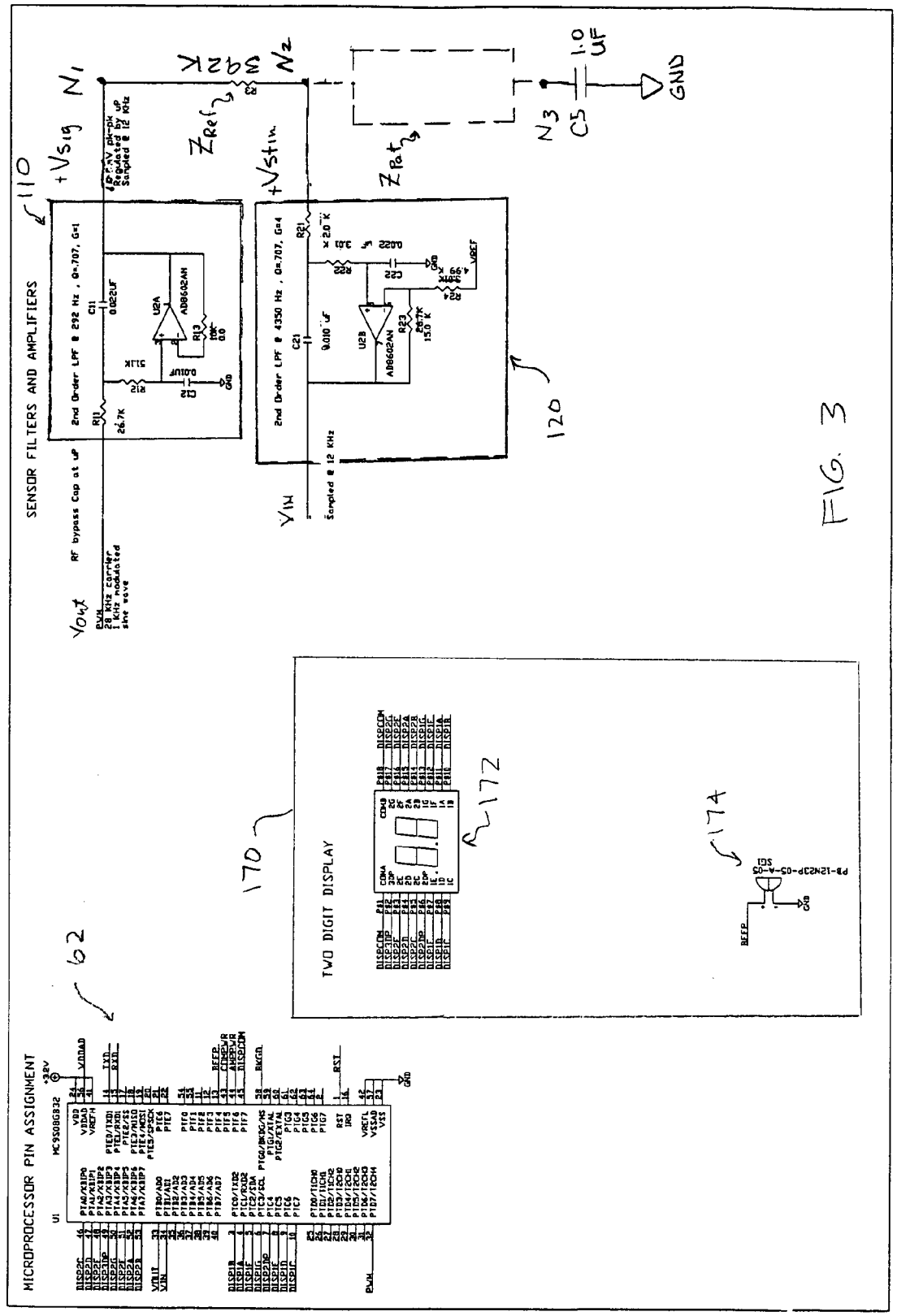
FIG. 3 is a schematic circuit diagram of a circuit incorporated in the apparatus of FIG. 2, according to an embodiment of the invention.

The operation of the apparatus 50 is described in conjunction with FIG. 3.

FIG. 3 is a schematic circuit diagram of a circuit 100 incorporated in the apparatus 50 of FIG. 2, according to an embodiment of the invention. The circuit 100 includes a microprocessor 62, a low-pass filter 110, the reference impedance $Z_{Ref}$, an amplified low-pass filter 120, the first node $N_1$, the second node $N_2$, and the third node $N_3$.

In one embodiment, the microprocessor 62 is a Motorola© MC9S08GB32 8-bit microcontroller unit that includes RAM and flash memory. The memory of the microprocessor 62 provides the memory function of the digital storage 64 of the apparatus 50. The microprocessor 62 includes a high-current line Vout. The microprocessor 62 is powered by a DC power source, such as a 3-volt battery (not shown).

The low-pass filter 110 is an active second-order low-pass filter having parameters including a 292 cutoff frequency, Q=0.707, and a gain of one. The parameters of the low-pass filter 110 are selected to provide the divider signal $V_{Sig}$ in response to VOut as described below. The reference impedance $Z_{Ref}$ is a 3.92 K ohm resistor element. In an alternative embodiment, the reference impedance $Z_{Ref}$ includes a reactive element, such as a capacitor. The capacitor may be selected to approximately equal parasitic capacitance of a test lead and/or an electrically conductive drive mechanism of a handpiece. The amplified low-pass filter 120 is an active second-order, low-pass filter having parameters including a 4350 cutoff frequency, Q=0.707, and a gain of four. The amplified low-pass filter 120 provides functions of both the low-pass filter 68 and the amplifier 66 of FIG. 2. As described in reference to the low-pass filter 68, the filtering parameters of the amplified low-pass filter 120 are selected to remove higher-order components of noise in the stimulation signal $V_{Stim}$ for more efficient demodulation. As described in reference to the amplifier 66, the amplifying parameters of the amplified low-pass filter 120 are selected to provide improved resolution of the stimulation voltage $V_{Stim}$ and aid in noise filtration. The proximity indicator 170 includes a digital display 172 operable to display two digits and a hepatic indicator 174 operable to produce a "beeping" sound.

Connections of the components of the schematic circuit diagram of the device 100 are indicated with reference to the pin labels of the microprocessor 62. As with FIG. 2, the reference impedance $Z_{Ref}$ is coupled between the first node $N_1$ and the second node $N_2$, the patient impedance $Z_{Pat}$ is coupled between the second node $N_2$ and the third node $N_3$. The third node $N_3$ is indicated as a ground or common point. The second node $N_2$ and third node $N_3$ are configured for electrically coupling the tip of the dental instrument in the root canal and the electrode coupled with a body tissue of the patient. The stimulation signal $V_{Stim}$ is defined between the second node $N_2$ and the third node $N_3$. A blocking capacitor C5 is included between the third node $N_3$ and ground to block DC current through the patient, and is illustrated as 1.0 microfarads.

The microprocessor 62 includes the lookup table stored its memory. The microprocessor 62 further includes operability that generates a single-frequency signal $V_{out}$ at pin 32, and that receives the stimulation signal $V_{Stim}$ at pin 34 for digital possessing. The digital processing includes demodulating the stimulation signal $V_{Stim}$, comparing the demodulated stimulation signal $V_{Stim}$ and the reference signal $V_{Sig}$, and generating a proximity signal from a stored lookup table. The demodulating includes removing noise from the stimulation signal $V_{Stim}$, which includes application of at least one of a synchronous demodulation algorithm, a fast Fourier transform, a single frequency fast Fourier transform, and a convolving algorithm. The noise removed may include noise from a dental handpiece that drives the dental instrument. The digital processing further includes automatically updating the proximity signal at least once each second, and preferably at least ten times each second. The proximity signal is generated in response to the comparison of the demodulated stimulation signal $V_{Stim}$ and the divider signal $V_{Sig}$.

The microprocessor 62 further includes operability that in cooperation with the low-pass filter 110 generates the reference signal $V_{Sig}$. The microprocessor 62 includes operability that generates a 28 KHz carrier that pulse-width-modulates to a 1 KHz sine wave signal $V_{out}$. The low-pass filter 110 smoothes the 1 KHz sine wave signal $V_{Out}$ and reduces its amplitude to a preselected amplitude the divider signal $V_{Sig}$, which is 100 mV peak-to-peak in the embodiment illustrated in FIG. 3. In an alternative embodiment, the microprocessor 62 may be configured to include a plurality of frequencies in the reference signal $V_{Sig}$ if advantageous for indicating proximity of the tip of the dental instrument to an apical foramen.

The microprocessor 62 also further includes an internal analog-to-digital converter that detects and samples (digitizes) the divider signal $V_{Sig}$ and the stimulation signal $V_{Stim}$. In an alternative embodiment, a separate analog-to-digital converter may be used to detect and sample the divider signal $V_{Sig}$ and the stimulation signal $V_{Stim}$, and provide digitized signal inputs to the microprocessor 62 for signal processing.

Figure 4:
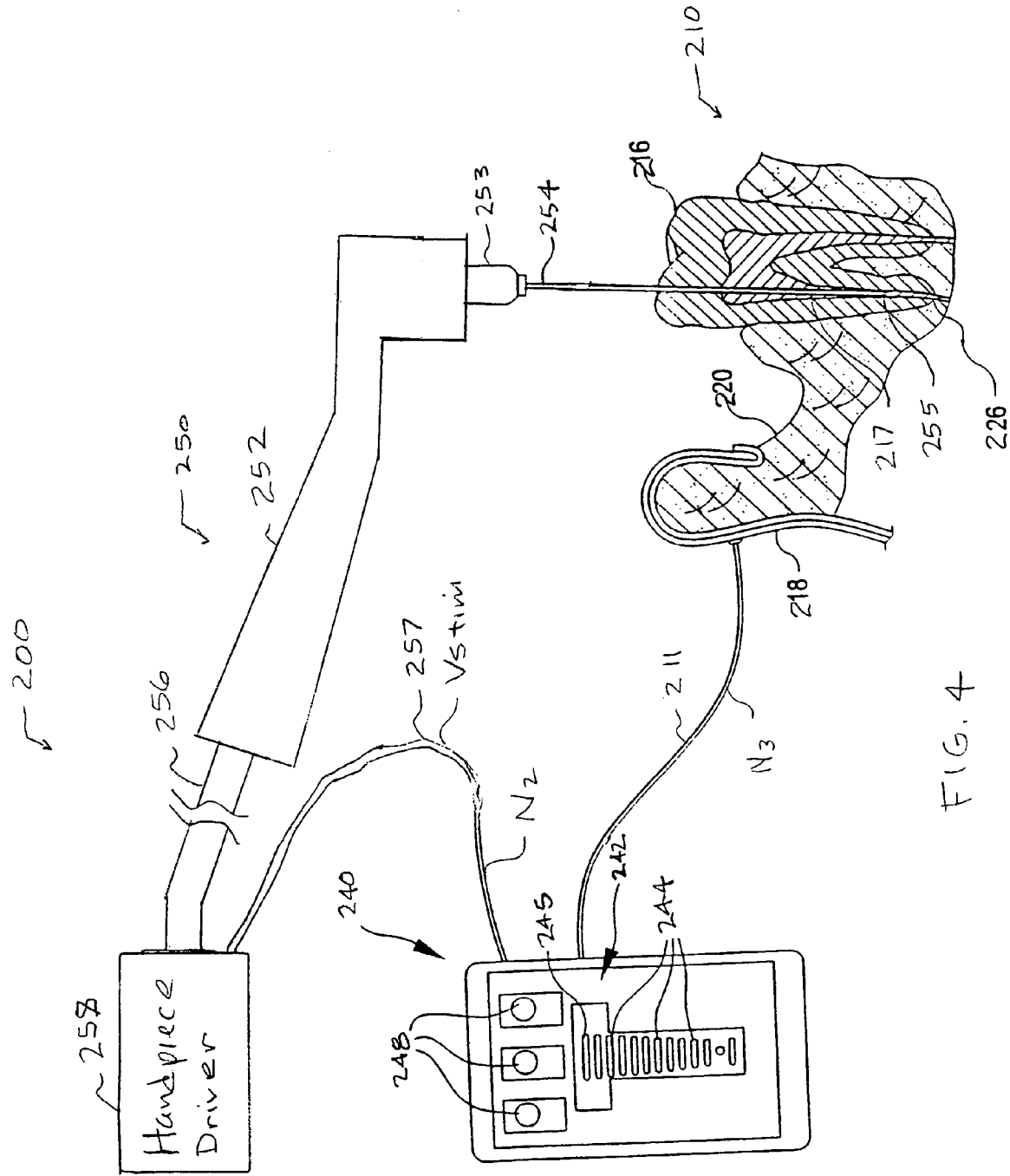
FIG. 4 is a perspective view of a system incorporating the apparatus of FIG. 2, according to an embodiment of the invention

FIG. 4 is a perspective view of a system 200 incorporating the apparatus 50 in FIG. 2, according to an embodiment of the invention. The system 200 includes an apical foramen indicator 240, and a dental handpiece 250.

The apical foramen indicator 240 includes the apparatus 50 of FIG. 2, which may be implemented by the circuit 100 of FIG. 3. The apical foramen indicator 240 also includes a display 242 as a proximity indicator presenting selected apical foramen location information to a dental/medical practitioner.

The dental handpiece 250 may be a traditional dental handpiece comprising a separate, typically stationary, handpiece driver 258 coupled to a handheld portion 252 by an electrically conductive path 256. Alternatively, the dental handpiece 250 may be a battery driven cordless handpiece that incorporates the handpiece driver, and any other configuration. The dental handpiece 250 includes a chuck 253 that removeably engages the conductive dental instrument 254 having the tip 255. The driver 258 drives the dental instrument 254, and is mechanically coupled to the chuck 253. At least a portion of the mechanical coupling between the driver 258 and the chuck includes the electrically conductive path 256. The handpiece coupler 257 may be connected to the electrically conductive path 256 at the driver 258, the handheld portion 252, or in some other manner, preferably using an existing electrically conductive pathway. The handpiece coupler 257 carries the divider signal $V_{Sig}$ of FIG. 2, and is at the second node $N_2$ of FIG. 2.

The patient 210 is illustrated with an electrically conductive "lip clip" 218 attached to the patient's lip 220, and the tip 255 of a dental instrument 254 in the root canal 217 of the tooth 216 at a distance from the apical foramen 226. The lip clip 218 is coupled by a ground coupler 211 to the indicator 240, and is at the third node $N_3$ of FIG. 2. The portion of the patient 210 between the tip 255 and the lip clip 218 is represented as $Z_{Pat}$ in FIG. 2. The indicator 240 may include an isolation capacitor (not shown) coupled to the ground coupler 211 for protection or convenience of the patient 210.

The display 242 can be any desired display capable of presenting apical foramen location data to the dental/medical practitioner. For example, in this and other embodiments, the display 242 can include lights 244 and 245 that can operate in a single mode, a persistent mode, or a logarithmic March mode. In the single mode, an end light 245 can represent the point where the tip 255 of the dental instrument 254 is proximate to the tooth's apical foramen 226 or is substantially close. The other lights 244 can indicate a relative distance or a dimension between the tip 255 of a dental instrument 254 and the apical foramen 226 by their proximity to the end light 245. Thus, as the tip 255 of the dental instrument 254 approaches the tooth's apical foramen 226, single lights 244 are turned "on" and then "off," and appear to march toward the end light 245. In the persistent mode, the lights 244 and 245 can indicate the distance of the tip 255 of the dental instrument 254 to the apical foramen 226 in a similar manner to the single light mode except the lights are not turned "off" as the tip of a dental instrument continues toward the apical foramen. In the logarithmic march mode, the number of lights 244 and 245 turned "on" can indicate a proximity or a distance between the tip 255 of a dental instrument 254 and the apical foramen 226.

In other embodiments of the indicator 240, the lights of the display 242 can be color-coded as desired to provide the dental/medical practitioner an easily recognizable indication of the apical foramen's location. Additionally or alternatively, the display 242 can include any desired sound to indicate proximity of the tip 255 of the dental instrument 254 to the apical foramen 226. For example, the display can provide beeps that can indicate proximity between the tip 255 of the dental instrument 254 and the apical foramen 226 based on the tone of the beep, the number of beeps or time between multiple beeps. In still other embodiments, the display can be a backlit liquid crystal display that presents text to the dental/medical practitioner or the display can be a video display that presents images to the dental/medical practitioner.

Still referring to FIG. 4, in this and other embodiments, the apical foramen indicator 240 can include mode buttons 248 for selecting a lookup table appropriate for the patient's tooth and for changing how the apical foramen location data is displayed to the dental/medical practitioner. Thus, a dental/medical practitioner can quickly change tooth maps as desired. In addition, the dental/medical practitioner can receive the apical foramen location data in a manner that they are most comfortable.

In operation, the lip clip 218 is placed on the patient's lip 220 and the ground coupler 211 is connected to the apical foramen indicator 240. The indicator 240 is coupled to the handpiece 250 with the coupler 257, which delivers the stimulation voltage $V_{Stim}$ to the electrically conductive path 256 in the handheld portion 252 of the handpiece and the correspondingly to the dental instrument 254. The conductive path between the tip 255 of the dental instrument 254 in the root canal 217 and the lip clip 220 includes both resistive and capacitive (reactive) components of $Z_{Pat}$ that correlate the patient impedance $Z_{Pat}$ with proximity to the apical foramen 226. As the tip 255 is moved along the root canal 217 toward or away from the apical foramen 226, the patient impedance $Z_{Pat}$ changes, thus changing the stimulation voltage $V_{Stim}$. The indicator 240 compares the stimulation voltage $V_{Stim}$ and the divider signal voltage $V_{Sig}$ as previously described, and indicates the proximity of the tip 255 to the apical foramen 226. The indicator 240 provides proximity indication while the dental instrument 254 is in operation because the microprocessor 62 of FIG. 2 includes operability that removes noise from the stimulation voltage $V_{Stim}$ introduced by operation of the handpiece 250.

Lookup Table

An aspect of the invention includes a correlation parameter that correlates a comparison of the divider signal $V_{Sig}$ and the stimulation signal $V_{Stim}$ with a proximity of the tip of the dental instrument in a root canal to the apical foramen. In an embodiment of the invention, the correlation parameter is empirically derived from testing one or more teeth. The correlation parameter can be embodied in a lookup table, an equation, or in some other form usable by the microprocessor 62 for translating a comparison of the divider signal $V_{Sig}$ and the stimulation signal $V_{Stim}$ into the proximity signal $V_{Prox}$. While the following describes generation of a lookup table, an equation or other correlating parameter may be generated in a similar manner.

The lookup table stored in the digital storage 64 of FIG. 2 includes at least one table correlating a comparison of the divider signal $V_{Sig}$ and the stimulation signal $V_{Stim}$ with proximity of the tip of the dental instrument in a root canal to the apical foramen. The correlation of the divider signal $V_{Sig}$ and the stimulation signal $V_{Stim}$ in effect measures a Thevenin equivalent of the root canal. A lookup table is used to correlate the Thevenin equivalent of the root canal with proximity of the tip of the dental instrument in the root canal to the apical foramen with by clinical studies and live studies.

The lookup table may be generated in any method suitable for producing a correlation between the patient impedance $Z_{Pat}$ and proximity of the tip 255 to the apical foramen 226, which is reflected in a comparison of the stimulation voltage $V_{Stim}$ and the divider signal voltage $V_{Sig}$. Such methods include clinical trials and bench testing. In bench testing, a setup similar to FIG. 4 may be used with a reference tooth and a lip model that mimics impedance of tissue surrounding a tooth. In both methods, the tip 255 is placed at a location in the root canal 217, the stimulation voltage $V_{Stim}$ and the divider signal voltage $V_{Sig}$ compared, and physical determination of proximity of the tip to the apical foramen made based on an x-ray or other known means. The comparison is then correlated with the physically determined proximity, and the correlation entered in the lookup table. The tip 255 location is then changed, and another correlation entered into the lookup table. This method is continued until a satisfactory granularity in the lookup table is achieved. The proximity may include a percentage of the root canal length, or a dimension, such as millimeters from the apical foramen 226. Since the patient impedance $Z_{Pat}$ varies depending on the type and structure of a tooth, and between patients, results from several trials may be combined into a single lookup table. In an alternative embodiment, a plurality of lookup tables may be stored in the digital storage 64 of FIG. 2, and the apparatus 50 provide for selection of a lookup table by the dental/medical practitioner.

It is generally accepted that the resistive component between the apical foramen and an electrode coupled to body tissue of the patient, such the patient's lip or skin, is approximately 2K ohms. The conductive pathway includes the nerve and blood vessel lying between. When the tip of the dental instrument initially enters the root canal from the tooth enamel portion of the tooth, it is further generally accepted that the resistive component between the root canal and an electrode coupled with the patient's lip is approximately 3K ohms. The patient impedance $Z_{Pat}$ also has a reactive component. Depending on several factors, the change in the patient impedance $Z_{pat}$ along the root canal 217 may or may not be linear or otherwise predictable. If the clinical and bench studies show resistance in the most valid qualifier of apical foramen location, then the lookup table may be built using only the resistive component of the patient impedance $Z_{Pat}$. Alternatively, if the clinical and bench studies show that impedance, resistive plus capacitive (reactive) components, is the most valid quantifier of apical foramen location, then the lookup table may be built using both the resistive and capacitive components of the patient impedance $Z_{Pat}$.

In preparing the lookup table, corruption of the patient impedance $Z_{Pat}$ may be introduced by elements in the stimulation signal $V_{Stim}$ pathway outside of the patient. The corruption typically is introduced by the leads and by components of the apparatus 50 of FIG. 2 in the stimulation signal $V_{Stim}$ pathway. The corruption is typically capacitive, and may be removed in determining the patient impedance $Z_{Pat}$ if resistive and capacitive components are found to be the most valid qualifier. Since the couplers 211 and 256 are made of metal wires, and the electrical conductive path 256 is metal, there effectively is no resistance in the conductive path contributed to $Z_{Pat}$ other than by the patient. However, there may be significant capacitance (reactive) corruption contributed to $Z_{Pat}$ by the couplers 211 and 256 of FIG. 4. In addition, there may be significant capacitive corruption introduced by the low-pass filter 68 and amplifier 66 of FIG. 2. This capacitive corruption contribution to the patient impedance $Z_{Pat}$ may vary depending on the type and configuration of dental handpiece 250 being used.

The capacitive corruption introduces a phase shift. Therefore, different handpiece 250 and apparatus 50 are expected to contribute different capacitive corruption to the patient impedance $Z_{Pat}$. The corruption for a particular handpiece and apparatus may be characterized and/or calibrated by opening the patient connection, i.e., the second node N2 and the third node N3, and recording the impedance as a baseline for the apical foramen measurements. The data used to build the lookup table may then be compensated for the corruption impedance in the testing system. Along the same line, a lookup table furnished with the indicator 240 of FIG. 4 may be compensated for the corruption characteristics of the system 200.

Although the present invention has been described in considerable detail with reference to certain preferred embodiments, other embodiments are possible. Therefore, the spirit or scope of the appended claims should not be limited to the description of the embodiments contained herein. It is intended that the invention resides in the claims hereinafter appended. The various embodiments of the invention may be implemented as a sequence of computer implemented steps or program modules running on a computing system and/or as interconnected machine logic circuits or circuit modules within the computing system. The implementation is a matter of choice dependent on the performance requirements of the computing system implementing the invention. In light of this disclosure, it will be recognized by one skilled in the art that the functions and operation of the various embodiments disclosed may be implemented in software, in firmware, in special purpose digital logic, or any combination thereof without deviating from the spirit or scope of the present invention.

What is claimed is:

1. An apparatus to determine the proximity of a dental instrument to a tooth's apical foramen while the instrument is in the tooth's canal, the apparatus comprising:
   a handpiece that includes:
       a dental instrument operable to remove tissue from a tooth of the patient,
       a handpiece driver operable to drive the dental instrument via a mechanical coupling between the handpiece driver and the dental instrument, and
       an electrically conductive path that includes at least a portion of the mechanical coupling between the dental instrument and the handpiece driver;
   a signal generator coupleable to body tissue of a patient and to the handpiece, wherein, while the signal generator is coupled to the body tissue and the handpiece, the signal generator generates a divider signal that is used to determine the proximity of the dental instrument to the tooth's apical foramen, and that travels the electrically conductive path; and
   a microprocessor coupleable to the handpiece and that, while coupled to the handpiece and while the instrument removes tissue from the patient's tooth,
       senses a stimulation signal that includes the divider signal modified by the impedance of the patient's body,
       demodulates the stimulation signal to isolate the stimulation signal from electrical noise received via the electrically conductive path between the dental instrument and the handpiece driver, and
       compares the stimulation signal to the divider signal generated by the signal generator.

2. The apparatus of claim 1, wherein the divider signal includes an amplitude and a frequency.

3. The apparatus of claim 1, wherein:
   the divider signal has an amplitude and a frequency, and
   the microprocessor compares the amplitude of the divider signal generated by the signal generator to an amplitude of the stimulation signal.

4. The apparatus of claim 1, further comprising a reference impedance coupled to the signal generator and the handpiece such that the reference impedance and the handpiece are arranged in series relative to each other, and the signal generator generates a divider signal across a combination of the reference impedance, the handpiece and the body tissue, wherein the reference impedance is known.

5. The apparatus of claim 4, wherein the reference impedance essentially consists of a resistive element.

6. The apparatus of claim 4, wherein the reference impedance comprises a resistive element and a reactive element.

7. The apparatus of claim 1, wherein in response to comparing the stimulation signal to the divider signal generated by the signal generator, the microprocessor generates a proximity signal that represents the proximity of the dental instrument to the tooth's apical foramen.

8. The apparatus of claim 7 wherein the proximity signal is generated from a look-up table that is stored in an apparatus.

9. The apparatus of claim 7 wherein the proximity signal is generated from an equation that is stored in an apparatus and executed by the microprocessor.

10. The apparatus of claim 1, further comprising an analog-to-digital converter that digitizes the stimulation signal.

11. The apparatus of claim 1, wherein:
    the divider signal has an amplitude and a frequency, and
    the microprocessor determines a phase of the stimulation signal relative to the divider signal generated by the signal generator.

12. The apparatus of claim 1, further comprising a signal conditioner that includes a low-pass noise filter to isolate the stimulation signal.

13. The apparatus of claim 12, wherein the signal conditioner includes an amplifier to amplify the stimulation signal.

14. The apparatus of claim 1, wherein the proximity indicator includes a haptic device.

15. The apparatus of claim 1, wherein the divider signal consists essentially of a single frequency.

16. The apparatus of claim 1 wherein the microprocessor executes a synchronous demodulation algorithm to demodulate the stimulation signal from electrical noise received via the electrically conductive path between the dental instrument and the handpiece driver.

17. The apparatus of claim 1 wherein the microprocessor performs a fast Fourier transform of the stimulation signal to demodulate the stimulation signal from electrical noise received via the electrically conductive path between the dental instrument and the handpiece driver.

18. The apparatus of claim 1 wherein the microprocessor performs a single-frequency fast Fourier transform of the stimulation signal to demodulate the stimulation signal from electrical noise received via the electrically conductive path between the dental instrument and the handpiece driver.

19. The apparatus of claim 1 wherein the microprocessor executes a convolving algorithm to demodulate the stimulation signal from electrical noise received via the electrically conductive path between the dental instrument and the handpiece driver.

20. A method for indicating the proximity of a dental instrument to a tooth's apical foramen, the method comprising:
    generating a divider signal across a combination of body tissue of a patient and a handpiece, wherein the handpiece includes:
        a dental instrument disposed in the tooth's root canal,
        a handpiece driver to drive the instrument via a mechanical coupling between the handpiece driver and the dental instrument, and
        an electrically conductive path that includes at least a portion of the mechanical coupling between the driver and instrument,
        wherein the combination includes the handpiece's electrically conductive path and the body tissue arranged in series relative to each other, and wherein the divider signal is used to determine the proximity of the dental instrument to the tooth's apical foramen;
    passing the divider signal through the electrically conductive path;
    impeding the signal with the body tissue;
    while the dental instrument removes tissue from the tooth, sensing a stimulation signal that includes the divider signal modified by the impedance of the patient's body tissue;

demodulating the stimulation signal to isolate the stimulation signal from electrical noise received via the electrically conductive path; and comparing the stimulation signal to the divider signal.

21. The method of claim 20, further comprising impeding the divider signal with a reference impedance that includes a resistive element.

22. The method of claim 20, further comprising impeding the divider signal with a reference impedance that includes a reactive element.

23. The method of claim 20, wherein generating the divider signal includes generating a signal that includes an amplitude and a frequency.

24. The method of claim 23 wherein the stimulation signal includes an amplitude and comparing the stimulation signal to the divider signal includes comparing their amplitudes.

25. The method of claim 23 wherein comparing the stimulation signal to the divider signal includes comparing a phase of the stimulation signal relative to a phase of the divider signal.

26. The method of claim 23 wherein the stimulation signal includes an amplitude and comparing the stimulation signal to the divider signal includes comparing their amplitudes and a phase of the stimulation signal relative to a phase of the divider signal.

27. The method of claim 20, wherein the divider signal consists essentially of a single frequency.

28. The method of claim 20, wherein sensing the stimulation signal includes amplifying the stimulation signal.

29. The method of claim 20, wherein demodulating the stimulation signal includes filtering noise from the stimulation signal.

30. The method of claim 20 wherein demodulating the stimulation signal includes performing at least one of the following: a synchronous demodulation algorithm, a fast Fourier transform, a single frequency fast Fourier transform, and a convolving algorithm.

31. The method of claim 20 further comprising generating a proximity signal based on the signal comparison.

32. The method of claim 31 further comprising indicating a proximity of the dental instrument to the apical foramen based on the proximity signal.

33. The method of claim 31 wherein generating a proximity signal includes retrieving data from a lookup table that correlates at least one signal comparison with a proximity of the dental instrument to the apical foramen.

34. The method of claim 31 wherein generating a proximity signal includes executing an equation that correlates at least one signal comparison with a proximity of the dental instrument to the apical foramen.

35. The method of claim 31, wherein indicating the proximity of the dental instrument to the apical foramen includes updating the proximity signal.

36. An apparatus to determine the proximity of a dental instrument to a tooth's apical foramen while the instrument is in the tooth's canal, the apparatus comprising:

a handpiece that includes:
  a dental instrument operable to remove tissue from a tooth of the patient,
  a handpiece driver operable to drive the dental instrument via a mechanical coupling between the handpiece driver and the dental instrument, and
  an electrically conductive path that includes at least a portion of the mechanical coupling between the dental instrument and the handpiece driver;
a signal generator coupleable to body tissue of a patient and to the handpiece, wherein, while the signal generator is coupled to the body tissue and the handpiece, the signal generator generates a divider signal across the body tissue and the electrically conductive path, wherein the divider signal generated by the signal generator passes through the handpiece driver to the dental instrument; and
a microprocessor coupleable to the handpiece and that, while coupled to the handpiece and while the instrument removes tissue from the patient's tooth,
  senses a stimulation signal that includes the divider signal modified by the impedance of the patient's body,
  demodulates the stimulation signal to isolate the stimulation signal from electrical noise received via the electrically conductive path between the dental instrument and the handpiece driver, and
  compares the stimulation signal to the divider signal generated by the signal generator.

37. A method for indicating the proximity of a dental instrument to a tooth's apical foramen, the method comprising:

generating a divider signal across a combination of body tissue of a patient and a handpiece, wherein the handpiece includes:
  a dental instrument disposed in the tooth's root canal,
  a handpiece driver to drive the instrument via a mechanical coupling between the handpiece driver and the dental instrument, and
  an electrically conductive path that includes at least a portion of the mechanical coupling between the driver and instrument,
  wherein the combination includes the handpiece's electrically conductive path and the body tissue arranged in series relative to each other;
passing the divider signal through the handpiece driver to the dental instrument;
impeding the signal with the body tissue;
while the dental instrument removes tissue from the tooth, sensing a stimulation signal that includes the divider signal modified by the impedance of the patient's body tissue;
demodulating the stimulation signal to isolate the stimulation signal from electrical noise received via the electrically conductive path; and
comparing the stimulation signal to the divider signal.

* * * * *